United States Patent [19]

Minetti

[11] Patent Number: 4,945,107

[45] Date of Patent: Jul. 31, 1990

[54] INSECT ATTRACTANT

[75] Inventor: Dawn C. Minetti, Wykoff, N.J.

[73] Assignee: American Cyanamid Company, Stamford, Conn.

[21] Appl. No.: 267,246

[22] Filed: Nov. 8, 1988

Related U.S. Application Data

[63] Continuation-in-part of Ser. No. 129,501, Dec. 7, 1987, abandoned.

[51] Int. Cl.$^5$ .............................................. A01N 43/08
[52] U.S. Cl. ..................................................... 514/473
[58] Field of Search ........................................ 514/473

[56] References Cited

U.S. PATENT DOCUMENTS

| 4,087,525 | 5/1978 | Lovell | 514/401 |
| 4,179,446 | 12/1979 | Tumlinson, III et al. | 424/84 |
| 4,447,447 | 5/1984 | Hreschak et al. | 514/673 |
| 4,498,587 | 2/1985 | Hreschak et al. | 514/919 |

FOREIGN PATENT DOCUMENTS

| 0079727 | 7/1976 | Japan | 424/84 |
| 0133201 | 10/1981 | Japan | 424/84 |

Primary Examiner—Leonard Schenkman
Attorney, Agent, or Firm—Charles J. Fickey

[57] ABSTRACT

As an attractant composition for cockroaches, a furanone compound having the formula

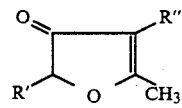

where R' is H or $CH_3$; R" is H, a straight chain or cyclic hydrocarbon moiety of 1 to 12 carbon atoms; oxy-alkyl and alkoxy groups, in a compatible, inert carrier; a poison bait food composition containing said attractant and a method of destroying cockroaches using said attractant.

8 Claims, No Drawings

INSECT ATTRACTANT

This application is a continuation-in-part of previously filed application Ser. No. 129,501 filed Dec. 7, 1987 now abandoned.

This invention relates to an attractant, for cockroaches. More particularly the invention relates to the use of a particular class of furanone derivatives as an attractant for cockroaches, to a poison bait food composition containing said furanones and a method for destroying cockroaches using said furanone derivatives.

The use of certain attractants for insects is known e.g. maltol and ethyl maltol (Japanese Pat. No. 52-38024); alcohols, aldehydes and lactones in plant extracts (Japanese Pat. No. 52-82729); and extracts of maple, birch and yeast (Japanese Pat. No. 42-82728). These substances however have shown low activity and had to be used in high concentrations.

In addition, Japanese Pat. No. 56-133201 discloses the use of derivatives of furanone, namely 3-hydroxy-4-methyl-2(5H)-furanone; 3-hydroxy-4,5-dimethyl-2(5H)-furanone and 5-ethyl-3-hydroxy-4-methyl-2 (5H)-furanone as insect attractants. These compounds are chemically related to the furanones of the present invention, but are sufficiently different that their activity is not predictable biologically. It has, in this regard, been found that the attractancy of the furanones of this invention are greatly superior to the prior art furanone derivatives for cockroaches.

It is further known from U.S. Pat. No. 4,447,447 to make a composition to guard the leaves of trees from infestation and eating by gypsy moth larvae. It is known that the larvae ascend the tree trunk at night to eat the leaves and descend to spend the day on the cooler ground. It is taught in the patent 4,447,447 to form a composition containing an aliphatic aldehyde having 2 to 7 carbon atoms; an organic sulfide, disulfide or mercaptan with from 1 to 14 carbon atoms; a diketo furan; a carboxylic acid of 1 to 14 carbon atoms; in a solvent, e.g. soybean oil or benzyl alcohol and optionally mixed with petroleum jelly. The composition is spread around the tree trunk as a band of material. It is said in the patent that the composition is effective in preventing the gypsy moth larvae from ascending the tree trunk because of its odor "but the actual mechanism has not been definitely established." Thus, while furaneol is one of the diketo furan ingredients of the composition, and is also within the class of furanones of the present invention, it is clearly not taught that furaneol would be an attractant when used alone, since the composition of the patent is clearly intended to be and is acting as a repellant.

It has now been surprisingly found that a particular class of furanone derivatives are attractants for cockroaches. The attractants of the present invention have the following general formula

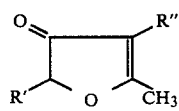

where R' is H, or CH$_3$; R" is H, a straight chain or cyclic hydrocarbon moiety of 1 to 12 carbon atoms; oxyalkyl and alkoxy. Exemplary R" groups are

—CH$_3$, C$_2$H$_5$, —C(=O)—CH$_3$, —C(=O)—CH$_3$—CH$_3$, —CH$_2$—O—CH$_3$,

—O—C(=O)—CH$_3$, —O—C(=O)—O—CH$_3$, —O—C(=O)—O—CH$_2$—CH$_3$,

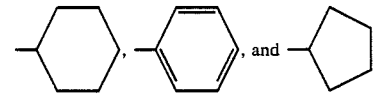

The insect attractants of the present invention are potent attractants of insect pests and highly superior attractants for cockroaches.

The furanone derivatives of the present invention may be used alone as an insect attractant, or may be prepared in the form of a solution or suspension in a suitable medium, or be mixed with or absorbed on a suitable carrier, or diluent. Additives, such as an emulsifier, a dispersing agent, a suspending agent, a spreader, or a stabilizer including antioxidants such as BHT and BHA may be used. The composition may be in the form of an oil, an emulsion, a hydrate, a powder, granules, tablets or microcapsules.

The terms attractant and bait have been widely used in the pesticidal art, and at times have been used interchangeably. As used in the present case, bait means a combination of a food and a pesticide, where inert ingredients may also be present to affect the physical consistency of the bait and its palatability to insects. The object is to induce insects to eat the bait so as to ingest the poison which acts within the insect to kill it. Insects can find the bait, but it does not necessarily attract them to its location.

An attractant is a chemical substance that actually attracts insects, over a distance, to the point where the attractant is located. It could be called a lure, a homing signal or a beacon.

Exemplary bait compositions are disclosed in U.S. Pat. Nos. 4,049,460 and 4,514,960. Examples of poisons are disclosed in U.S. Pat. Nos. 4,087,525 and 4,163,102. Suitable bait feeding stations are disclosed in U.S. Pat. No. 4,563,836 or D278,842.

It will of course be understood that the above are only exemplary.

An exemplary poisoned bait is a solid non-particulate, non-flowable, non-repellant, fully edible insecticide-bait composition, comprising a pentadienone hydrazone insecticide compound, a specific food attractant system, and a binder. A preservative is optionally added to the composition.

Pentadiene-3-one substituted amidinohydrazones are described by Tomcufcik, U.S. Pat. No. 3,878,201, as antimalrial and anti-tubercular agents. Lovell, U.S. Pat. Nos. 4,087,525 and 4,163,102—the disclosures of which are incorporated by reference thereto, describes the use of these compounds as insecticides. The insecticide compounds of the Lovell patents are generally represented by the formula:

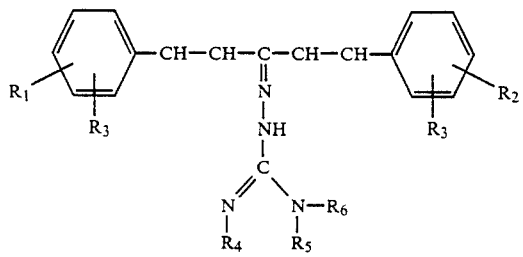

(I)

wherein $R_1$ and $R_2$ each represent hydrogen, halogen, the group —$CF_3$, $C_1$-$C_4$ alkyl, $C_1$-$C_4$ alkoxy, or $C_1$-$C_4$ alkylthio; $R_3$ is hydrogen or methyl, provided that when $R_3$ is methyl both $R_1$ and $R_2$ are also methyl; $R_4$ and $R_5$ represent hydrogen, $C_1$-$C_4$ alkyl or, when taken together, an alkylene group of 2 to 6 carbon or 1,2-cyclohexylene; $R_6$ is hydrogen or $C_1$-$C_4$ alkyl; and salts thereof.

Particularly useful compounds are those represented by the formula:

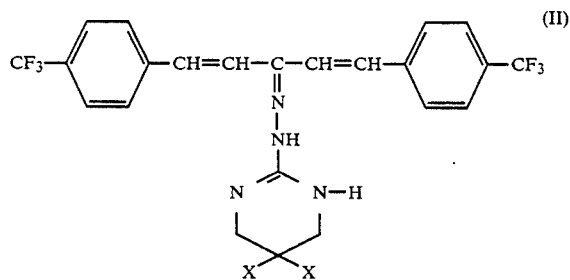

(II)

wherein X is hydrogen or methyl, e.g. the compound 1,5-bis(α, α, α-trifuloro-p-tolyl)-1,4-pentadien-3-one (1,4, 5,6-tetrahydro-5,5-dimethyl-2-pyrimidinyl)hydrazone. Wherein the group X is formula (II) are each methyl.

The insect attractant of the present invention may be used with the hydrazones previously described above or may be used with organophosphorous insecticides, carbamate type insecticides, pyrethoid type insecticides, hydrazone type insecticides, and the like, or a combination of insecticides. Some examples of commercial products which may be used are BAYGON (a carbamate); DURSBAN and DIAZONON (organophosphates); PYRETHRIN (a natural phrethroid); SUMITHRIN, TETRAMETHRIN, d-TRANS ALLETHRIN, and SBIO ALLETHRIN (synthetic pyrethroids). These insecticides may be incorporated in a bait that is a food substance which is intended to be eaten by the roaches, whereby the roaches also ingest the insecticide. The type of bait may be any which has been found to be palatable to roaches, such as described in U.S. Pat. Nos. 4,049,460 and 4,514,960 and copending, commonly assigned patent application Ser. No. 042,500, filed Apr. 27, 1987; and Ser. No. 933,331, filed Nov. 19, 1986.

The insect attractant may also be combined with insect hormone (e.g., juvenile hormone), chemical antifertility agents, other attractants (pheromone, sexual and feeding attractants) perfumes and antifungal agents.

The techniques for the use of the attractant also include inducing the pest to enter a trap which does not allow escape, leading the pest to an adhesive (paste), combining with insecticide as indicated earlier, and combining with antifertility agents and juvenile hormones that reduce the population density of the insects.

The furanone attractants of the present invention may also be used in a feeding station such as disclosed in U.S. Pat. No. 4,563,836 or D278,842. Such feeding stations have a base and cover with a solid bait placed in the center of the base and openings around the periphery of the base. The attractant may be mixed in the bait. Alternatively, the attractant may be deposited on the inner surface of the cover at the center thereof. It is advantage when the attractant is separate from the bait to mix it with an inert material that will adhere well to the surface of the cover. e.g. carbowax, or to impregnate paper or the like with a solution of the attractant which is then affixed to the cover.

The furanone attractants will generally be used as a 1 to 25% organic solvent solution, preferably 15% where the organic solvent is a lower glycol or acetone, e.g. propylene glycol. However, the furanone attractants can be solubilized by other solvents such as isopropanol (alcohols) or butyl carbitol (glycol ethers). When this solution is added to a bait, the amount of solution is from 0.01% to 10% of the total weight of the bait and attractant. The bait composition also comprises 0.1 to 3% pesticide and 87 to 99% food and inert ingredients, with the preferred range being 0.1% attractant, 2% pesticide and 97.9% food and inert ingredients.

The efficacy of the attractants is described in the following examples.

EXAMPLE I

4-Hydroxy-2,5-dimethyl-3(2H) furanone (furaneol)

Furaneol was first screened as a cockroach attractant. A total weight of 0.10 grams of furaneol was placed onto Whatmann #1 filter paper, then placed into a petri dish. The petri dish was placed into a nalgene tank 2'×2'×2.5' containing three cockroach haborages, each representing a random population of American roaches. Food, harborage and water were available to the roaches. Visual observation of the roaches activity was conducted for a sixty minute period. Furaneol caused increased roach activity for the length of the observation.

Further attractancy testing was conducted on Furaneol. One gram was placed onto Whatmann #1 filter paper, then placed into a greased, thirty-two ounce, wide mouth jar. A blank piece of filter paper was placed into the same type jar as a control. Both jars were placed at opposite corners of a 2'×2'×2.5' nalgene tank containing three harborages that represented a random population of American roaches. Food, harborage and water were available to the roaches. The jars remained in the tank overnight and a count of trapped roaches was made the following day. In each of three trials, there was a significant increase in roaches trapped in the jar containing furaneol. In the above series of tests, a commercially available attractant, sotolon, was also tested. Furaneol surpassed sotolon in efficacy.

EXAMPLE II

Tests were conducted to determine the level at which Furaneol should be incorporated into placebo COMBAT® bait, a commercially available bait, (essentially as described in copending, commonly assigned application Ser. No. 933,331) for field testing. The following bait compositions were made, incorporating furaneol as an attractant in the amounts of 1.5, 1.875, 2.5, 3.75, 7.5%, and no furaneol as a control.

| BAIT | |
|---|---|
| A | COMBAT ® + 1.5% furaneol |
| B | COMBAT ® + 1.875 |
| C | COMBAT ® + 2.5 |
| D | COMBAT ® + 3.75 |
| E | COMBAT ® + 7.5 |
| F | COMBAT ® |

In testing of the above baits, it was found that the attractancy of furaneol was effective in all of the above bait compositions.

EXAMPLE III-V

Primary Field Testing for Furaneol Attractant

OBJECTIVE - To determine field efficacy of furaneol as a cockroach attractant. The amount of furaneol used in the baits was set at 7.5%.

METHODS - Sampling was conducted using paired jar trapping, with one jar containing blank COMBAT ® bait and the other containing COMBAT ® bait plus 7.5% furaneol attractant. Jars were placed 18 to 24 inches apart, and left overnight in a suitable habitat. Captured cockroaches were counted, with age and sex noted, and released. Fresh baits were placed in the jars and the position reversed for the second night trapping. Catch was tallied in a similar manner for the second night. Baits were freshly made before each of the first two sampling periods so that the first day utilized one day old bait and the second night evaluated two day old baits. The third evaluation used two week old baits. Testing was conducted both indoors and outdoors.

Testing was conducted in a housing development in Alabama, and housing in Virginia.

EXAMPLE III

RESULTS - Furaneol attracted more individual cockroaches than the standard bait in 41 of 49 pairs of traps in Alabama. The results are shown in TABLE I. Species included the following:

TABLE I

| Sex/Age | Furaneol | COMBAT ® | Difference |
|---|---|---|---|
| *Periplaneta fuliginosa* - The Smokybrown Cockroach | | | |
| Males | 82 | 59 | 1.4x |
| Females | 40 | 25 | 1.6x |
| Nymphs | 98 | 52 | 1.9x |
| TOTAL | 220 | 136 | 1.6X |
| *Periplaneta americana* - The American Cockroach | | | |
| Male | 2 | 1 | 2.0x |
| Females | 16 | 8 | 2.0x |
| Nymphs | 4 | 2 | 2.0x |
| TOTAL | 22 | 11 | 2.0x |
| *Blattella germanica* - The German Cockroach | | | |
| Males | 10 | 3 | 3.3x |
| Females | 14 | 0 | xxxx |
| Nymphs | 24 | 1 | 24.0x |
| TOTAL | 48 | 4 | 12.0x |

EXAMPLE IV

At Virginia in the feed room of a poultry research facility, furaneol attracted more individual cockroaches in 13 to 15 pairs of traps. See Table II.

TABLE II

| Sex/Age | Furaneol | COMBAT ® | Difference |
|---|---|---|---|
| *Blatta orientalis* - The Oriental Cockroach | | | |
| Males | 19 | 4 | 4.8x |
| Females | 42 | 3 | 14.0x |
| Nymphs | 437 | 92 | 4.8x |
| TOTAL | 498 | 99 | 5.0x |

EXAMPLE V

At Virginia in basements of public housing units, furaneol attracted more individual cockroaches in 19 to 23 comparisons. See Table III.

TABLE III

| Sex/Age | Furaneol | COMBAT ® | Difference |
|---|---|---|---|
| *Periplaneta americana* - The American Cockroach | | | |
| Males | 35 | 7 | 5.0x |
| Females | 55 | 19 | 2.9x |
| Nymphs | 79 | 59 | 1.3x |
| TOTAL | 169 | 85 | 2.0x |

EXAMPLE VI

At Alabama, baits aged for two weeks and tested in a similar manner to the preceding Examples I through V showed furaneol to be more attractive in 5 of 6 paired comparisons. See Table IV.

TABLE IV

| Sex/Age | Furaneol | COMBAT ® | Difference |
|---|---|---|---|
| *Periplaneta fuliginosa* - The Smokybrown Cockroach | | | |
| Males | 20 | 12 | 1.7x |
| Females | 21 | 11 | 1.9x |
| Nymphs | 57 | 34 | 1.7x |
| TOTAL | 98 | 57 | 1.7x |

In the following Examples 3 milligrams and 10 milligrams of furaneol was applied to the inner dimple of bait trays of the type as shown in U.S. Pat. No. D278,842.

EXAMPLE VII

A field study for American cockroaches was conducted in Gainesville, Fla. using trays with bait (no attractant) versus trays with attractant plus bait. The results are shown in Table V.

TABLE V

| | Combat ® | Combat ® Plus Furaneol - 3 mg. |
|---|---|---|
| Adults | 5 | 39 |
| Nymphs | 1 | 0 |
| TOTAL | 6 | 39 |

| | Combat ® | Combat ® Plus Furaneol - 10 mg |
|---|---|---|
| Adults | 4 | 206 |
| Nymphs | 1 | 39 |
| TOTAL' | 5 | 245 |

EXAMPLE VIII

A field study for German cockroaches was conducted in Tampa, Fla. as described in Example VII. The results are shown in Table VI.

TABLE VI

| | Combat ® Plus |

TABLE VI-continued

|  | Combat ® Furaneol - 3 mg |  |
|---|---|---|
| TOTAL | 9 | 115 |
|  | Combat ® Plus Combat ® Furaneol - 10 mg |  |
| TOTAL | 24 | 159 |

EXAMPLE VII-XII

The following compounds were also tested as described in Example I and found to have attractancy activity as shown in Table VII. Sotolon, a close structurally related compound of the prior art, as described above (Japanese Pat. No. 56-133201) and furaneol are included for comparison.

TABLE VII

| Example | Attractant Compound | Insects Trapped Attractant | Control |
|---|---|---|---|
| VII | 4-hydroxy-2,5-dimethyl-3(2H)furanone acetate | 9 | 8 |
| VIII | 4,5-dihydro-2,5-diemthyl-4-oxo-3-furanyl methyl ester (carbonic acid) | 113 | 39 |
| IX | 4,5-dihydro-2,5-dimeemthyl-4-oxo-3-furanyl ethyl ester (carbonic acid) | 53 | 27 |
| X | 2-cyclohexy-5-methyl-3-(2H)furanone | 183 | 79 |
| XI | 4-acetyl-5-methyl-3-(2H) furanone | 223 | 71 |
| XII | 2,5-dimethyl-3-(2H) furanone | 16 | 9 |
| XIII | 4-hydroxy-2,5-dimethyl-3-(2H) furanone | 44 | 5 |
| IV | 3-hydroxy-4,5-dimethyl-2(5H)-furanone (Sotolon) | 2 | 0 |

I claim:

1. A method for attracting cockroaches which comprises placing a composition containing an effective amount of 4-hydroxy-2,5-dimethyl-3(2H) furanone and an inert diluent is an area inhabited by cockroaches.

2. A method of claim 1 wherein said attractant is used as a 15% organic solution.

3. The method of claim 1 wherein said attractant is used in combination with an insecticide.

4. The method of claim 3 wherein said insecticide is a pentadienone hydrazone.

5. The method of claim 3 in which said attractant and insecticide are incorporated with a food carrier.

6. An attractant composition for cockroaches which comprises 4-hydroxy-1,5-dimethyl13(2H)-furanone in an inert diluent and an insecticide.

7. The composition of claim 6 wherein said insecticide is a pentadienone hydrazone.

8. The composition of claim 6 comprising in addition a food carrier.

* * * * *